(12) United States Patent
Giannopoulos et al.

(10) Patent No.: US 10,358,255 B2
(45) Date of Patent: Jul. 23, 2019

(54) CLAMSHELL CASE FOR HOLDING MEDICINE AND A MEDICINE APPLICATOR

(71) Applicant: Tac Life Systems LLC, Walpole, MA (US)

(72) Inventors: Peter Giannopoulos, Walpole, MA (US); Joshua J. DeLisle, Hanover, MA (US); Frank Nogueira, Boston, MA (US); Leo Manning, Dorchester, MA (US)

(73) Assignee: Tac Life Systems LLC, Walpole, MA (US)

( * ) Notice: Subject to any disclaimer, the term of this patent is extended or adjusted under 35 U.S.C. 154(b) by 195 days.

(21) Appl. No.: 15/290,651

(22) Filed: Oct. 11, 2016

(65) Prior Publication Data

US 2017/0137166 A1     May 18, 2017

Related U.S. Application Data

(60) Provisional application No. 62/240,996, filed on Oct. 13, 2015.

(51) Int. Cl.

| B65D 69/00 | (2006.01) |
|---|---|
| B65D 8/00 | (2006.01) |
| A61M 5/00 | (2006.01) |
| B65D 43/22 | (2006.01) |
| B65D 25/10 | (2006.01) |
| B65D 6/00 | (2006.01) |
| A61M 15/08 | (2006.01) |

(52) U.S. Cl.
CPC .............. *B65D 11/02* (2013.01); *A61M 5/002* (2013.01); *A61M 15/08* (2013.01); *B65D 11/20* (2013.01); *B65D 25/10* (2013.01); *B65D 43/22* (2013.01); *A61M 2209/06* (2013.01)

(58) Field of Classification Search
CPC ........ B65D 11/02; B65D 11/20; B65D 25/10; B65D 43/22; A61M 5/002; A61M 15/08; A61M 2209/06
USPC .................. 206/363, 438, 570, 571, 705; 220/4.22–4.25
See application file for complete search history.

(56) References Cited

U.S. PATENT DOCUMENTS

| 1,239,308 | A | * | 9/1917 | Scott | .................... | B65D 77/245 |
|---|---|---|---|---|---|---|
| | | | | | | 206/229 |
| 2,651,407 | A | * | 9/1953 | Blackman | ............ | B65D 25/105 |
| | | | | | | 206/366 |
| D282,281 | S | * | 1/1986 | Nitzsche | ...................... | D24/229 |
| 5,566,828 | A | * | 10/1996 | Claes | ..................... | A61M 5/003 |
| | | | | | | 206/1.5 |
| 6,029,816 | A | * | 2/2000 | Goodwin | ................ | A45C 11/34 |
| | | | | | | 206/214 |
| 8,479,919 | B2 | * | 7/2013 | Kaplan | ................ | B65D 51/002 |
| | | | | | | 206/438 |

(Continued)

*Primary Examiner* — Luan K Bui
(74) *Attorney, Agent, or Firm* — Brian M. Dingman; Dingman IP Law, PC

(57) ABSTRACT

A clamshell case with a first portion and a second portion that are connected by a hinge. The first portion has one or more structures that are each adapted to removably hold a medicine vial, and the second portion has one or more structures that are each adapted to removably hold the barrel of a medicine applicator. There is a releasable case closure system that releasably maintains the two portions in a closed position.

17 Claims, 20 Drawing Sheets

(56) References Cited

U.S. PATENT DOCUMENTS

| | | | |
|---|---|---|---|
| 2006/0169611 A1* | 8/2006 | Prindle | A61M 5/002 206/364 |
| 2015/0014210 A1* | 1/2015 | Priebe | A61J 1/03 206/571 |
| 2015/0164743 A1* | 6/2015 | Janson | B65D 21/0223 206/571 |

* cited by examiner

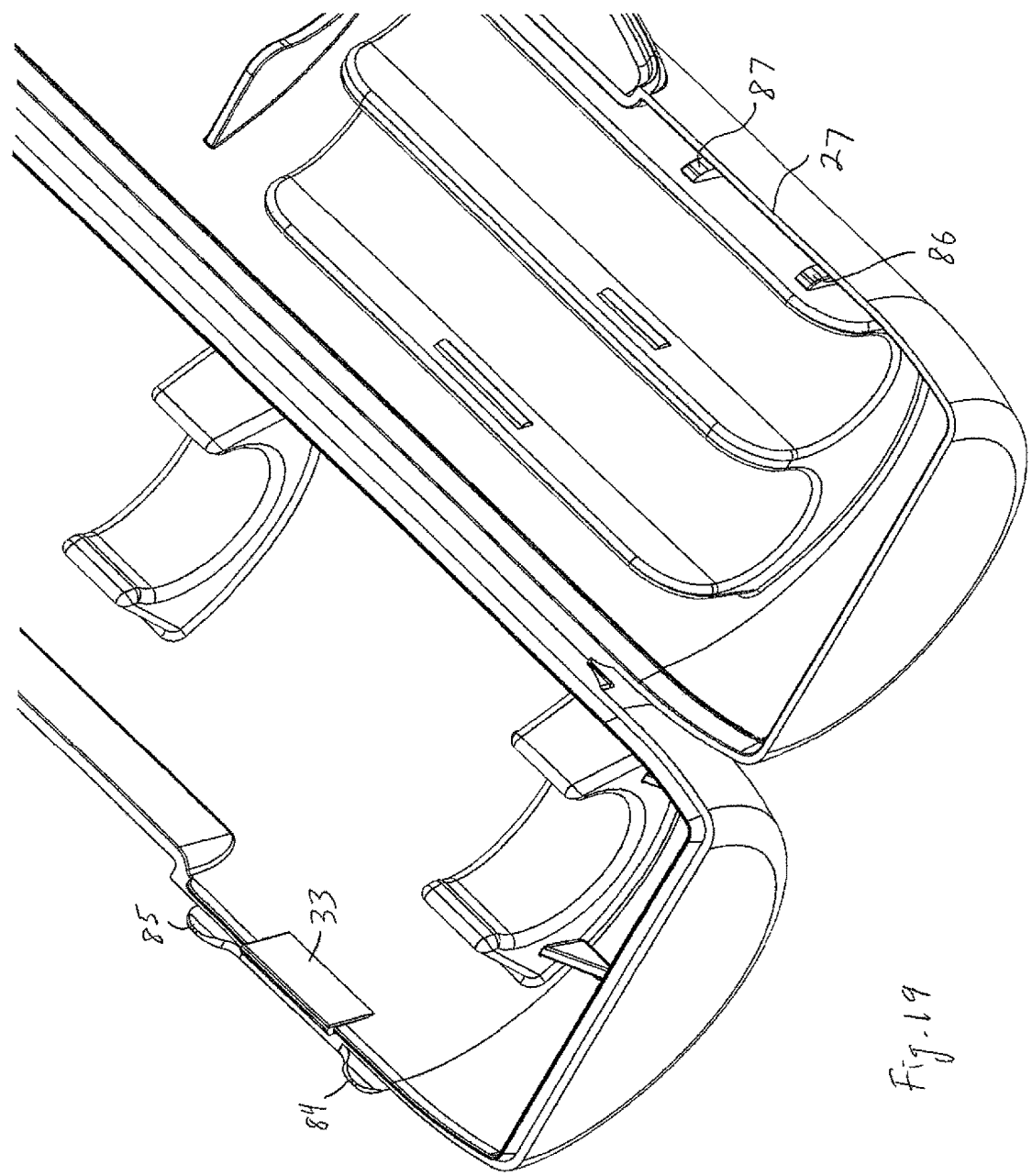

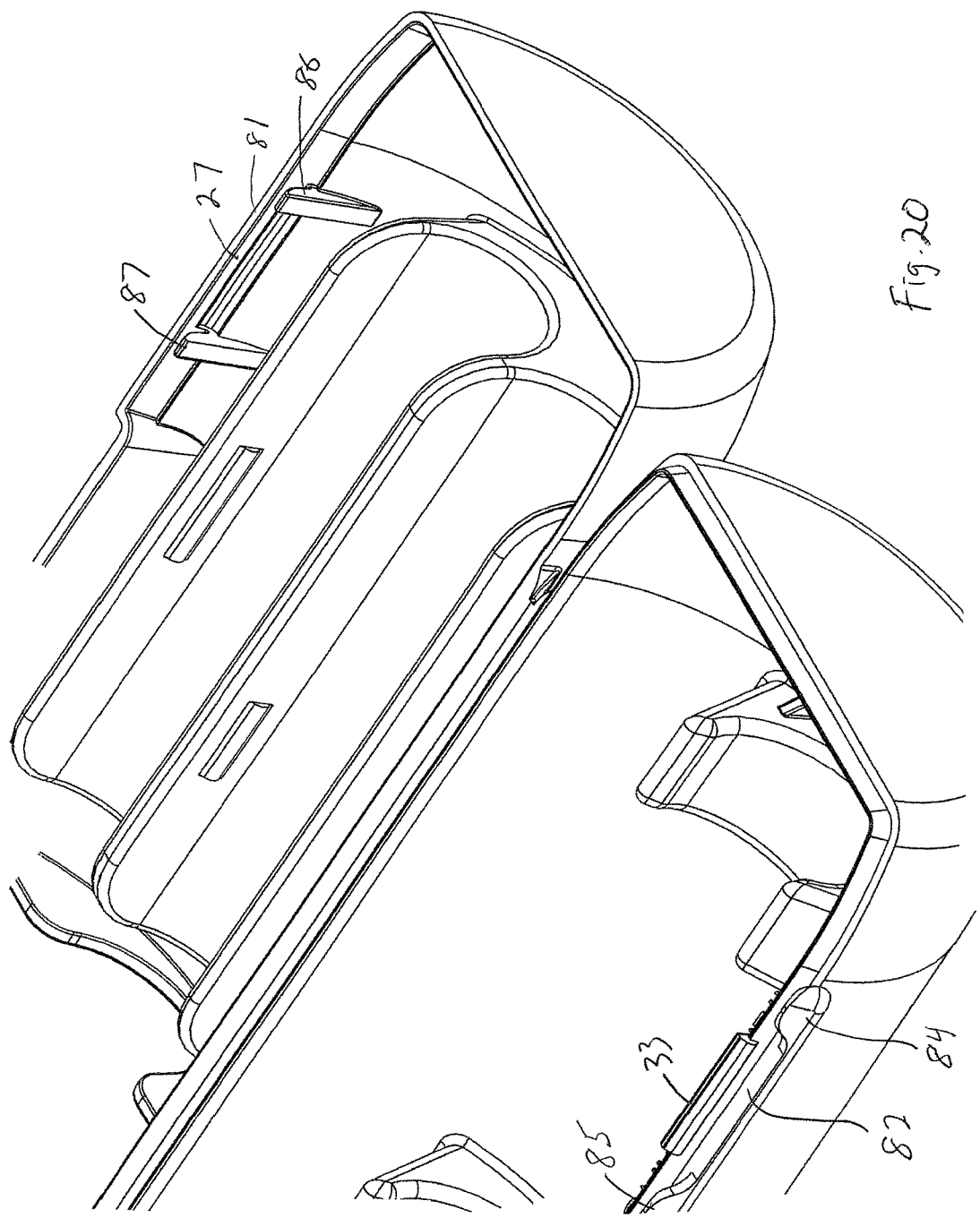

CLAMSHELL CASE FOR HOLDING MEDICINE AND A MEDICINE APPLICATOR

CROSS-REFERENCE TO RELATED APPLICATION

This application claims priority from Provisional Application 62/240,996, filed on Oct. 13, 2015, the disclosure of which is incorporated herein by reference.

BACKGROUND

Naloxone is an example of a medicine that sometimes needs to be carried by first responders such as police officers, firemen and EMTs. Naloxone comes in a small vial and can be administered with a nasal applicator/atomizer or a medicine atomizer/applicator. First responders thus need to carry one or more vials of naloxone (and/or other medicines) and one or more applicators. Often medicine vials are carried in a cardboard container in a uniform pocket, where they are subject to degradation.

SUMMARY

Featured in this disclosure is a clamshell-type case; a container that opens and closes. The case is constructed and arranged to hold medicine, and one or more applicators for the medicine. In the specific non-limiting embodiment shown in the drawings, the medicine is naloxone, which is a liquid that can be administered nasally or IV/IM. The applicator can be a syringe or a nasal applicator or any other type of applicator for the medicine that is carried in the case. The case is also constructed and arranged to be carried by a police officer, military, security, EMTs or other first responder in a pouch of the type that is often carried on the utility belt of such first responder. One example of an appropriate pouch is a pouch that is used to carry a pepper spray canister (e.g., an OC pouch), the pouch being a leather pouch with a top flap closure to allow for easy access. The case can be carried in such a pouch that is typically used for pepper spray.

The case in the non-limiting examples disclosed herein in detail is a hard-shell, one piece construction made by injection molding of an appropriate plastic such as polypropylene or the like. The case protects the medicine and the applicator(s) from degradation due to sunlight and weather. Also, the case provides crush and impact protection to the medicine and applicators, which is particularly important when medicines are in glass vials. Further, the case can be used to store the medicine and the applicator in a home or business or the like, and also is a convenient means to hold used components for disposal. The shape of the container fits into most hands and offers a secure grip when hands may be cold or wet. The container snaps shut, thus securing its contents.

In one aspect, the disclosure includes a clamshell case with a first portion and a second portion that are connected by a hinge. The first portion has one or more structures that are each adapted to removably hold a medicine vial, and the second portion has one or more structures that are each adapted to removably hold the barrel of a medicine applicator. There is a releasable case closure system that releasably maintains the two portions in a closed position. The portions may be generally semi-cylindrical.

The closure system may include a latch system that comprises a pair of latch tabs that have enlarged ends and are in one of the portions, and a pair of tab end receiving structures in mating parts of the other portion. The latch system may further comprise a pair of guide tabs located outside of and on either side of each latch tab. The latch system may further comprise a pair of posts proximate each tab receiving structure, where when the case is closed the guide tabs fit just outside of the posts to help properly align and seat the latch tab in the tab receiving structure.

The case may also include a case opening/closing flange comprising flange parts on each of the case portions. The opening/closing flange may allow the user to manipulate the case into the open or closed position, wherein from the closed position the user can push the flange parts apart in order to release the closure tabs from the tab receiving depressions and allow the case to open via the hinge.

The structures that are each adapted to removably hold a medicine vial may each comprise a saddle. There may be two essentially identical saddle vial holders that each have at least one small projection that is located such that it sits above the center of the vial when the vial is pushed into the saddle so that the vial is positively retained in the saddle.

The structures that are each adapted to removably hold the barrel of a medicine applicator may each comprise a saddle. There may be two spaced aligned saddles, wherein the saddles are each constructed and arranged to hold part of the barrel of a medicine applicator that can be used to inject the medicine, wherein the saddles are slightly deformed when a medicine applicator is pushed into them so that they tightly grip the medicine applicator, and wherein the saddles encompass more than 180° of the medicine applicator barrel so that the medicine applicator is positively retained in the saddles.

The clamshell case may further include an upstanding wall that in part defines an empty cavity that can be used to store a nasal atomizer or other medicine atomizer/applicator. The clamshell case may further include a top and a bottom, wherein the bottom has an essentially flat surface that allows the case to stand up on a flat surface, and wherein the top is more rounded than the bottom so that the case doesn't easily stand on its top end. The bottom end may have a taper leading to the essentially flat bottom surface, where the taper helps the case to be more easily inserted into and removed from a holder or pouch. The top may include one or more circumferential projecting rings that provide finger grips to allow the case to be grasped and removed from the holder or pouch, and wherein the rings provide a surface on which the case will roll generally in a circle if it is dropped on the ground, instead of rolling away from the user.

In another aspect the disclosure features a clamshell case with a first portion and a second portion that are connected by a hinge, wherein the first portion comprises one or more saddles that are each adapted to removably hold a medicine vial, and wherein the second portion comprises one or more saddles that are each adapted to removably hold the barrel of a medicine applicator, a releasable case closure system that releasably maintains the two portions in a closed position, wherein the closure system comprises a latch system that comprises a pair of latch tabs that have enlarged ends and are in one of the portions, and a pair of tab end receiving structures in mating parts of the other portion, and an upstanding wall that in part defines an empty cavity that can be used to store a nasal atomizer or other medicine atomizer/applicator.

The clamshell case can further include a case opening/closing flange comprising flange parts on each of the case portions, wherein the opening/closing flange allows the user to manipulate the case into the open or closed position, wherein from the closed position the user can push the flange parts apart in order to release the closure tabs from the tab receiving depressions and allow the case to open via the hinge. The clamshell case may have two essentially identical saddle vial holders that each comprise at least one small projection that is located such that it sits above the center of the vial when the vial is pushed into the saddle so that the vial is positively retained in the saddle.

In another aspect the disclosure features a clamshell case with a first generally semi-cylindrical portion and a second generally semi-cylindrical portion, where the two portions are connected by a living hinge. The first portion comprises two essentially identical saddle vial holders that are each adapted to removably hold a medicine vial and that each comprise at least one small projection that is located such that it sits above the center of the vial when the vial is pushed into the saddle so that the vial is positively retained in the saddle. The second portion comprises two spaced, aligned saddles that are each adapted to removably hold part of the barrel of a medicine applicator, wherein the saddles are constructed and arranged to hold a medicine applicator that can be used to inject the medicine, wherein the saddles are slightly deformed when a medicine applicator is pushed into them so that they tightly grip the medicine applicator, and wherein the saddles encompass more than 180° of the medicine applicator barrel so that the medicine applicator is positively retained in the saddles. There is a releasable case closure latch system that releasably maintains the two case portions in a closed position, wherein the latch system comprises a pair of latch tabs that have enlarged ends and are in one of the portions, and a pair of tab end receiving structures in mating parts of the other portion, wherein the latch system further comprises a pair of guide tabs located outside of and on either side of each latch tab and a pair of posts proximate each tab receiving structure, where when the case is closed the guide tabs fit just outside of the posts to help properly align and seat the latch tab in the tab receiving structure. There is a case opening/closing flange comprising flange parts on each of the case portions, wherein the opening/closing flange allows the user to manipulate the case into the open or closed position, wherein from the closed position the user can push the flange parts apart in order to release the closure tabs from the tab receiving depressions and allow the case to open via the hinge. The case has a top and a bottom, wherein the bottom has an essentially flat surface that allows the case to stand up on a flat surface, wherein the top is more rounded than the bottom so that the case doesn't easily stand on its top end, wherein the bottom end has a taper leading to the essentially flat bottom surface, where the taper helps the case to be more easily inserted into and removed from a holder or pouch, and wherein the top includes one or more circumferential projecting rings that provide finger grips to allow the case to be grasped and removed from the holder or pouch, and wherein the rings provide a surface on which the case will roll generally in a circle if it is dropped on the ground, instead of rolling away from the user. There is also an upstanding wall that in part defines an empty cavity that can be used to store a nasal atomizer or other medicine atomizer/applicator.

BRIEF DESCRIPTION OF THE DRAWINGS

Each of FIGS. 1-18 illustrate a case in accordance with one non-limiting example of the present disclosure, while FIGS. 19 and 20 illustrate aspects of a different example. Like numbers are used for like elements of the drawings.

FIGS. 19 and 20 are both partial views, illustrating a different closure system.

DETAILED DESCRIPTION

Figure 1:
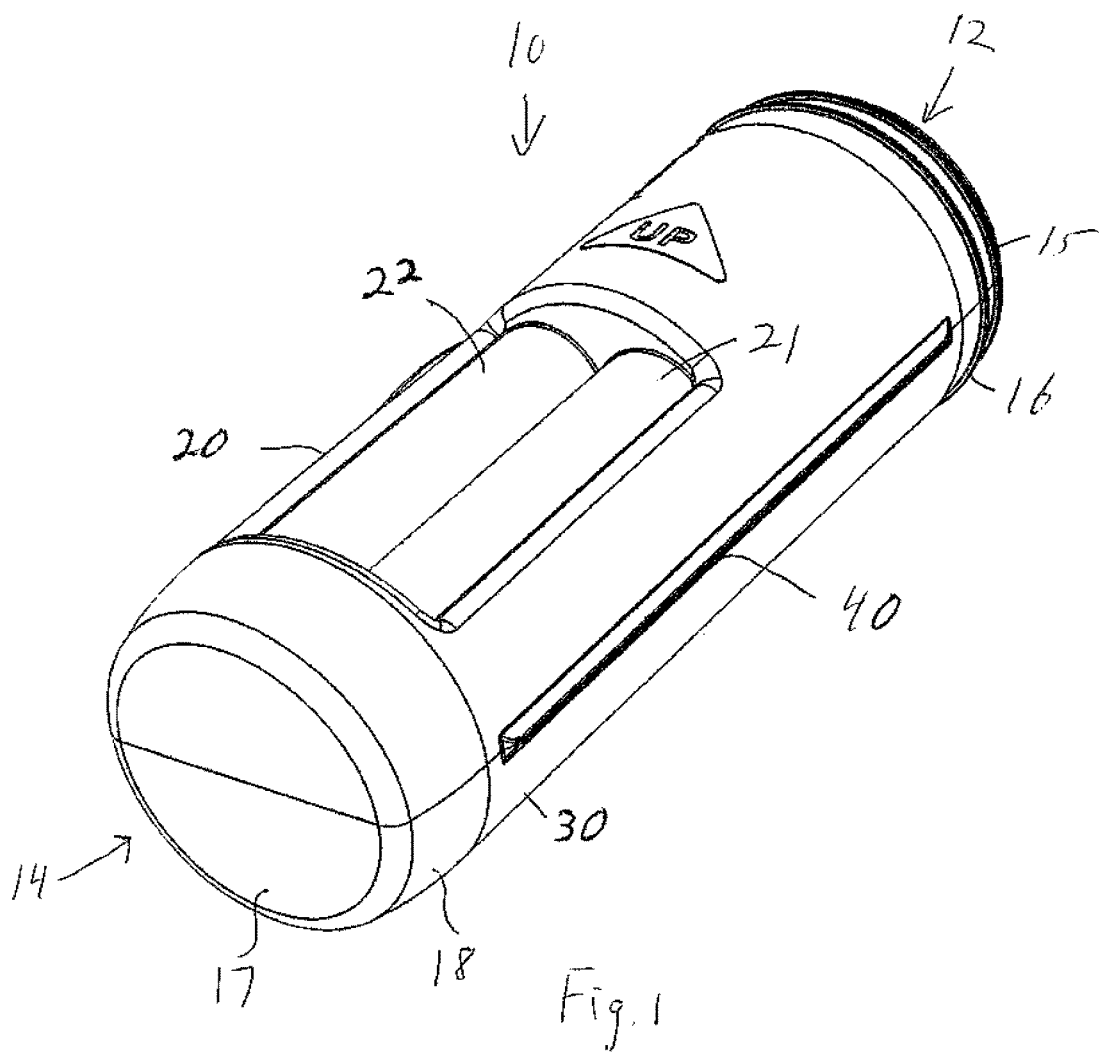
FIG. 1 is a perspective view of one side of a case in its closed position.
Figure 2:
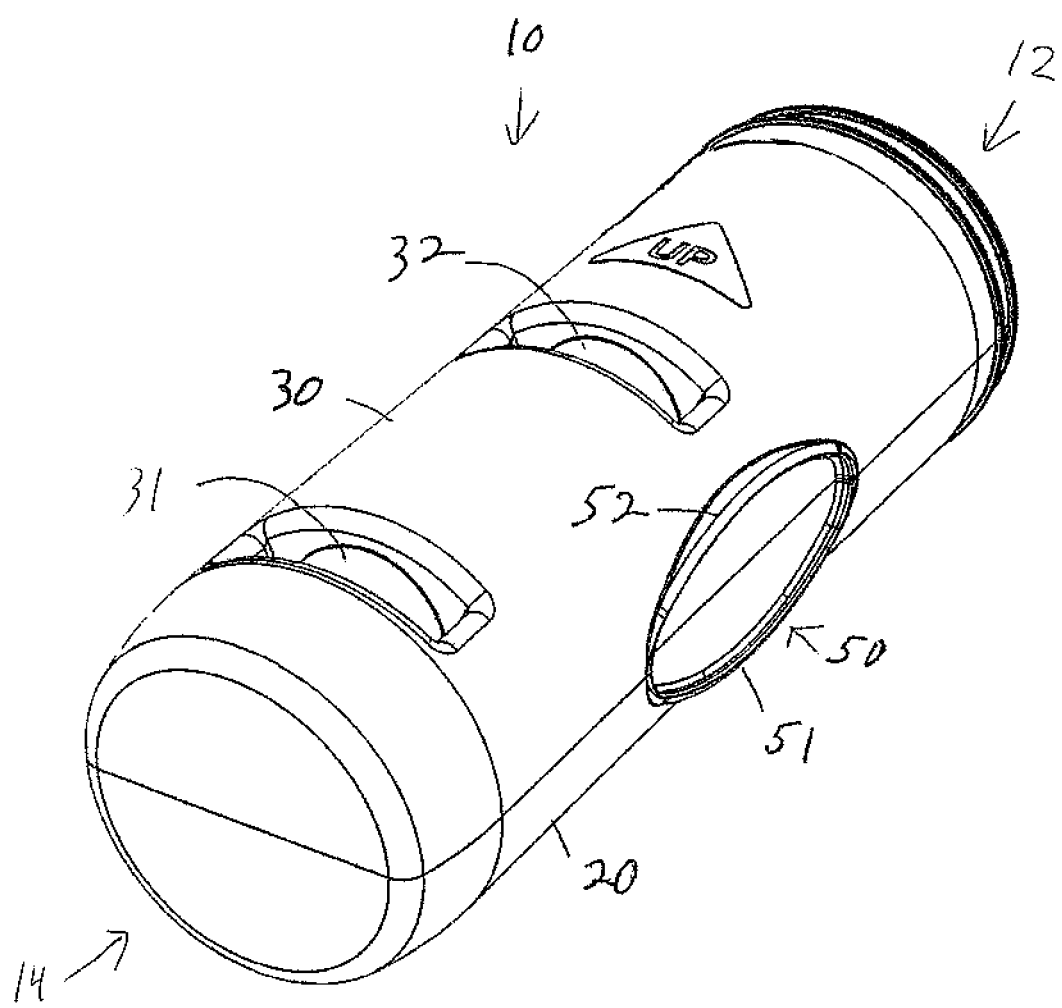
FIG. 2 is a perspective view of the other side of the case in its closed position.
Figure 3:
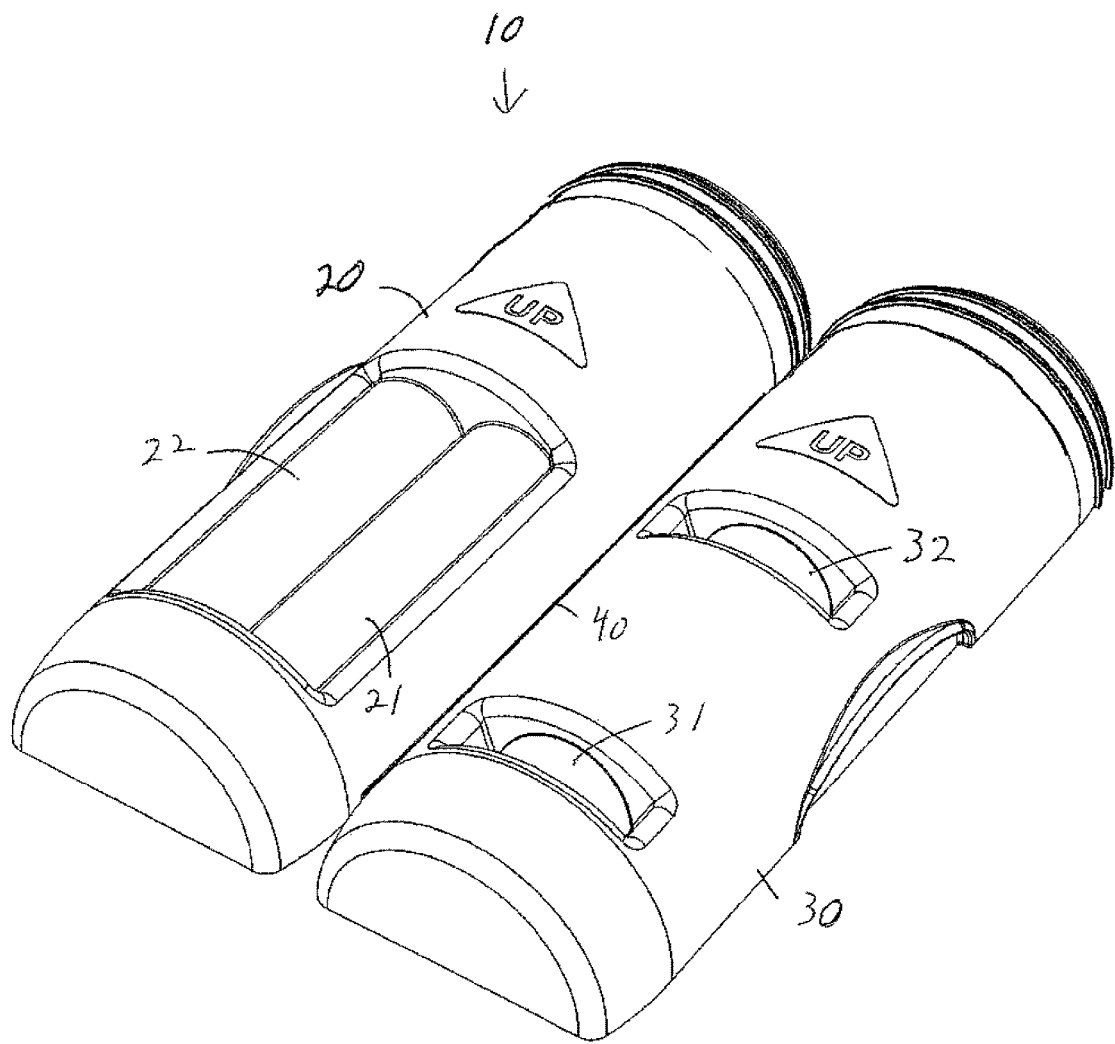
FIG. 3 is a perspective view of the outside of the case in the open position.
Figure 4:
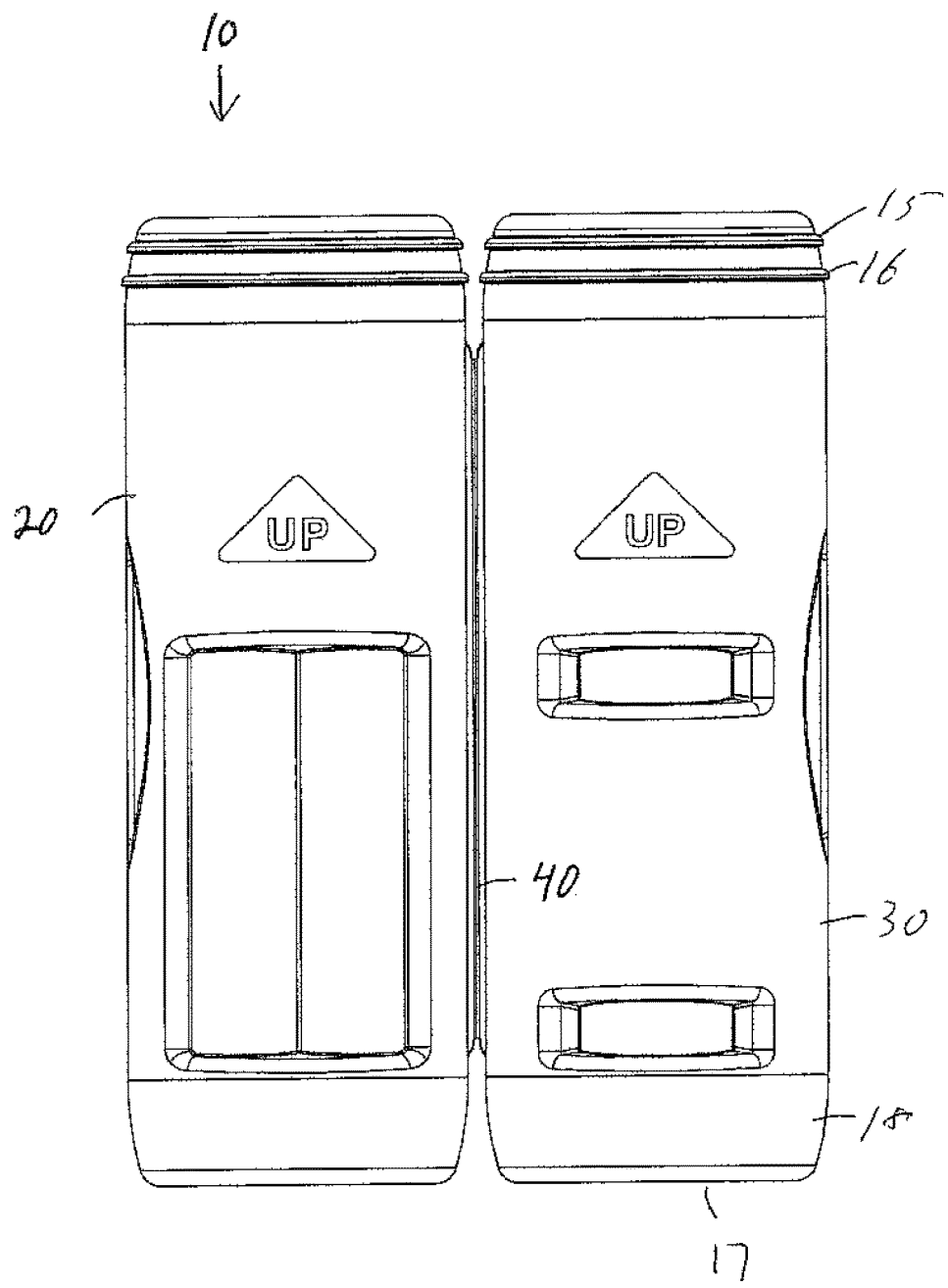
FIG. 4 is a top view of the outside of the case in the open position.
Figure 5:
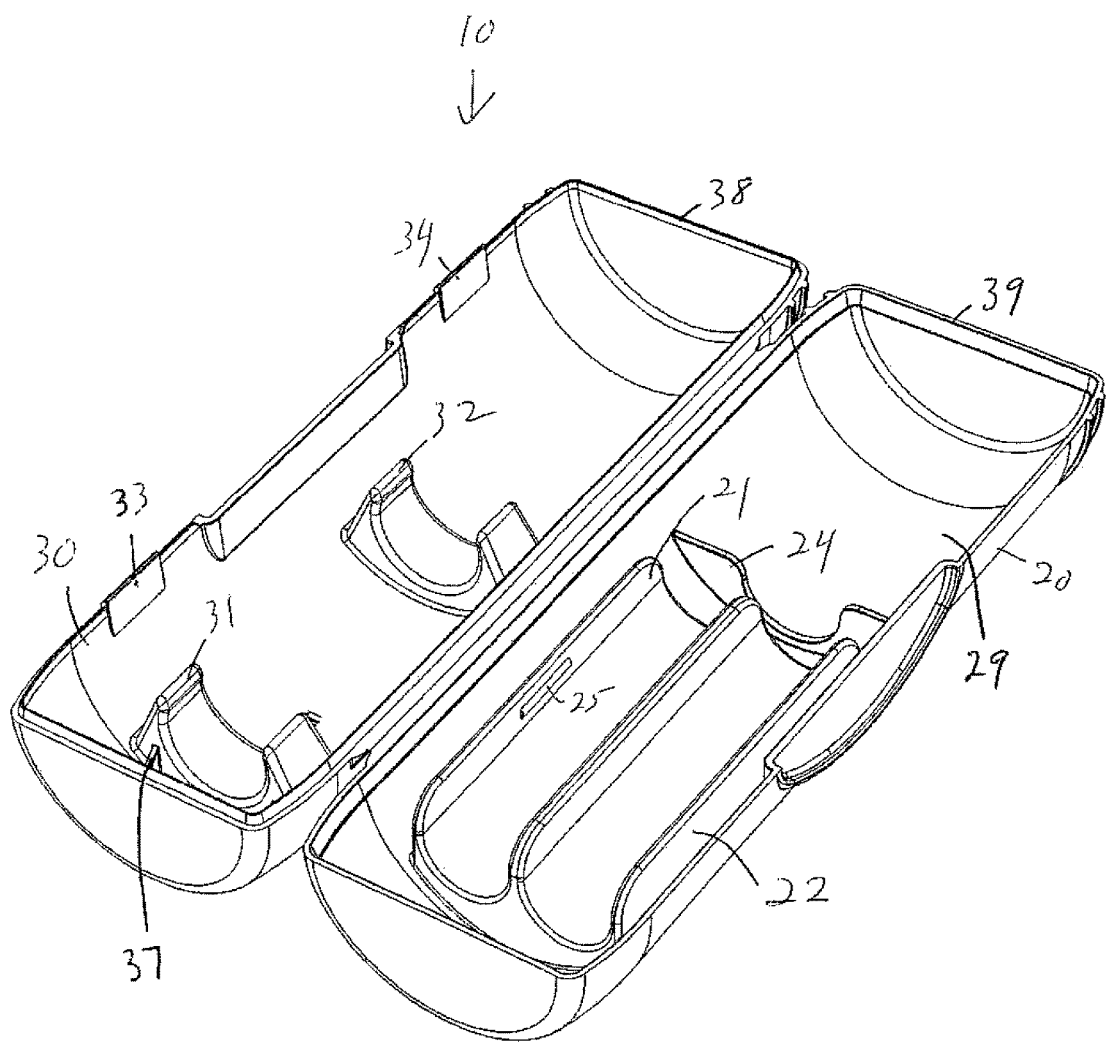
FIG. 5 is a perspective view of the inside of the case in the open position.
Figure 8:
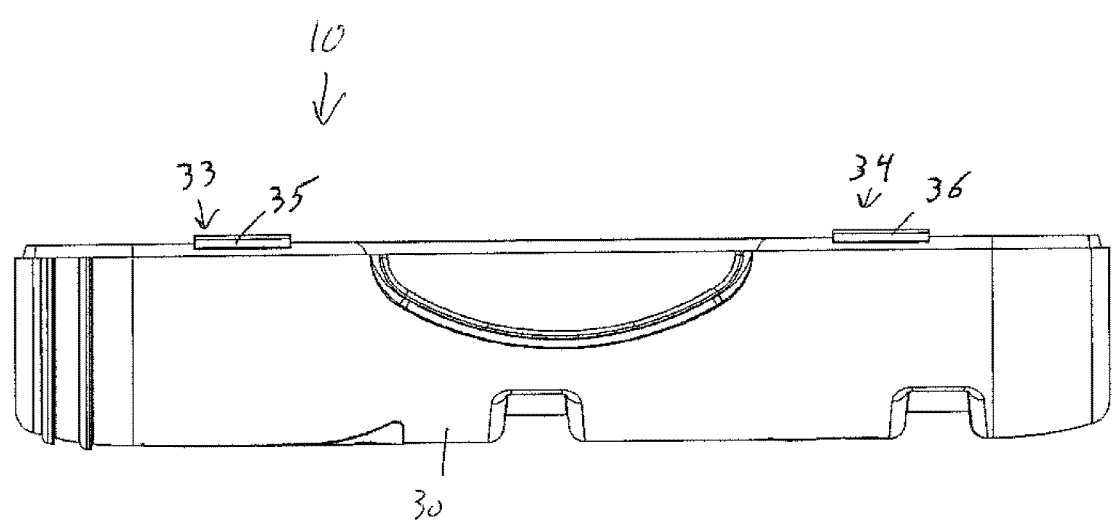
FIG. 8 is a left side view of the outside of the case in the open position.
Figure 9:
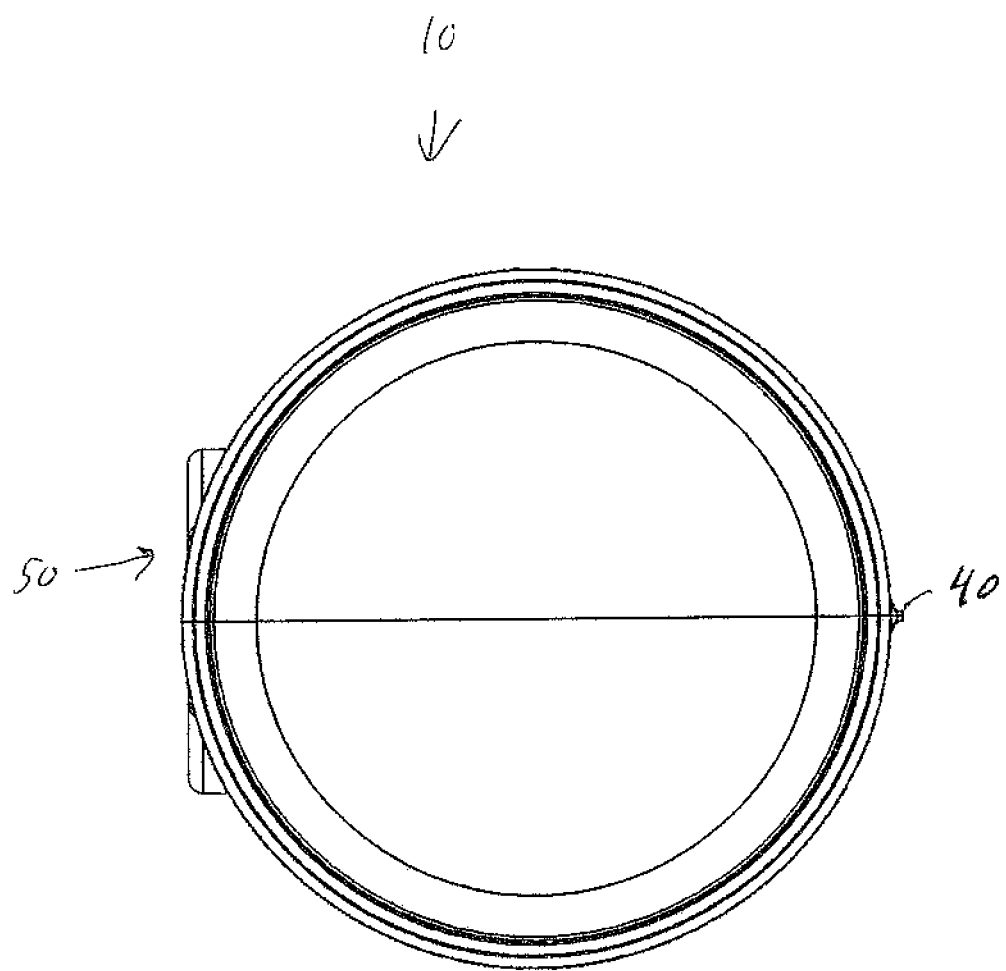
FIG. 9 is a top view of the closed case.
Figure 10:
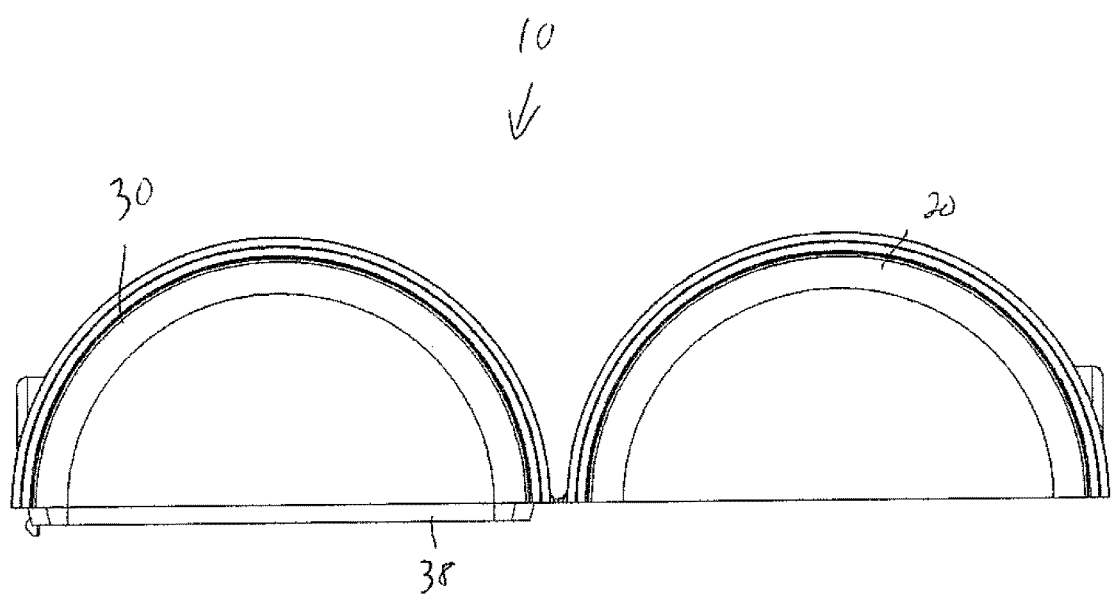
FIG. 10 is a top view of the outside of the case in the open position.
Figure 11:
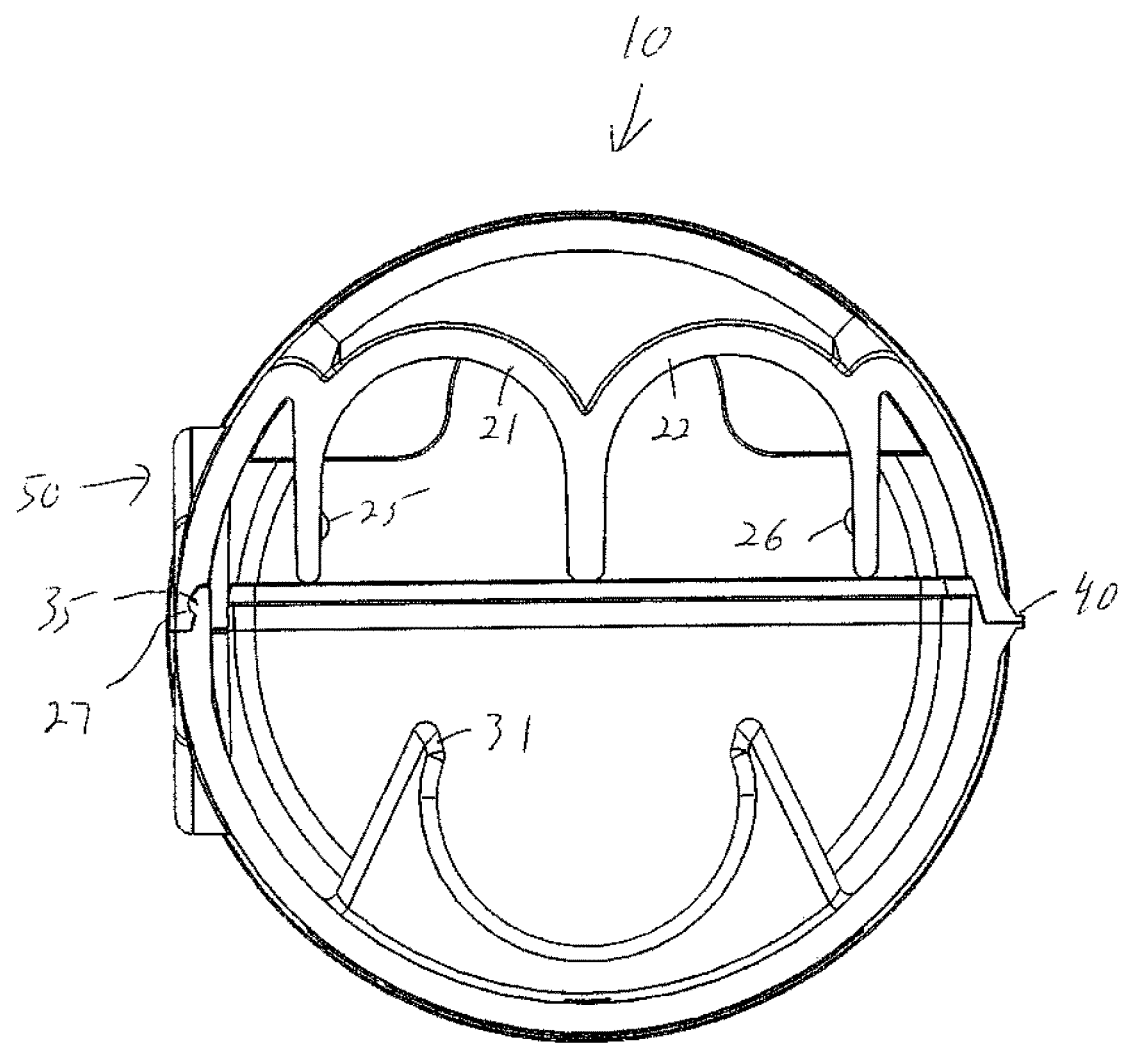
FIG. 11 is a cross-sectional view of the case.
Figure 12:
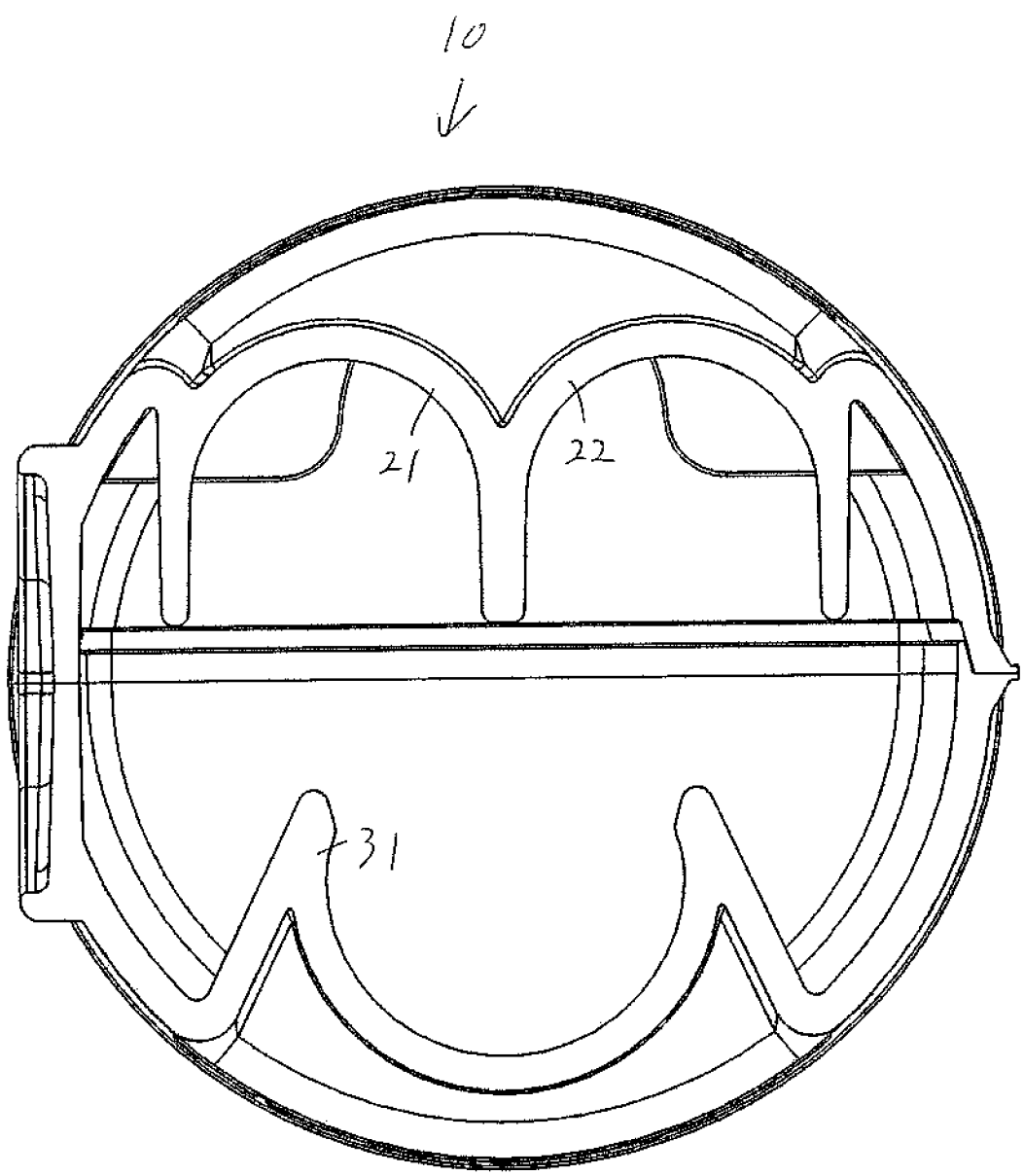
FIG. 12 is another cross-sectional view of the case.
Figure 13:
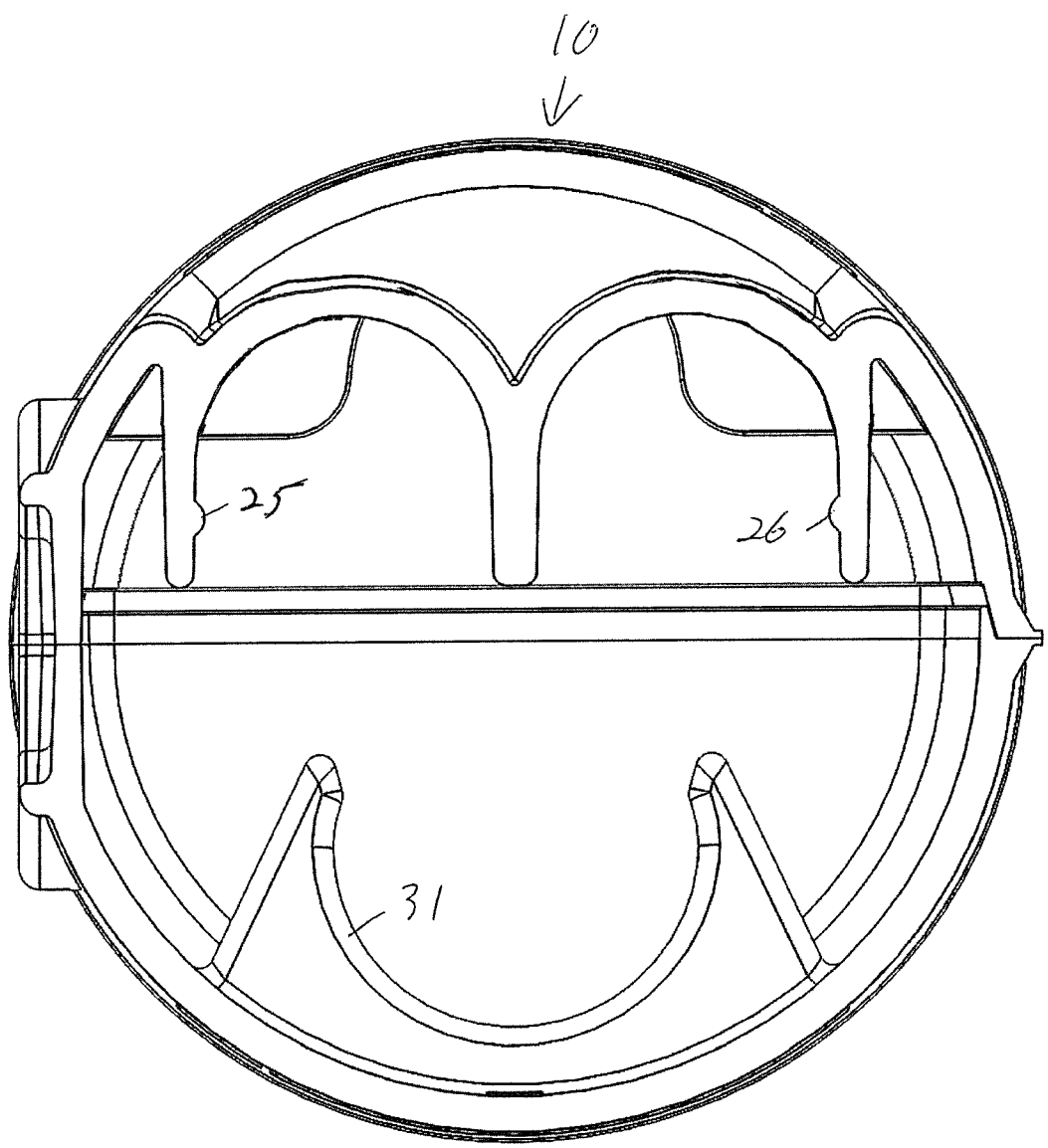
FIG. 13 is another cross-sectional view of the case.
Figure 14:
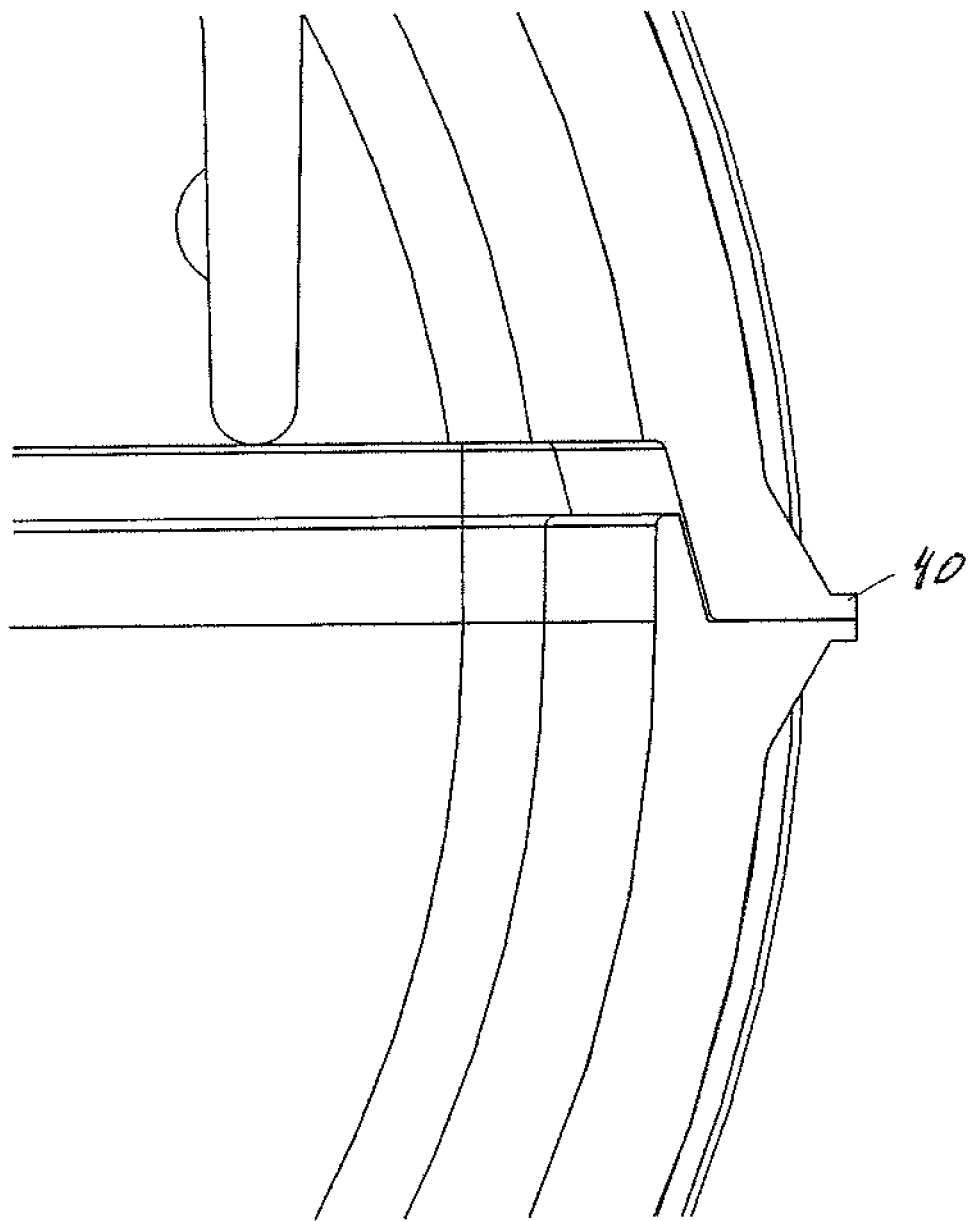
FIG. 14 is a cross-section through the hinge.
Figure 15:
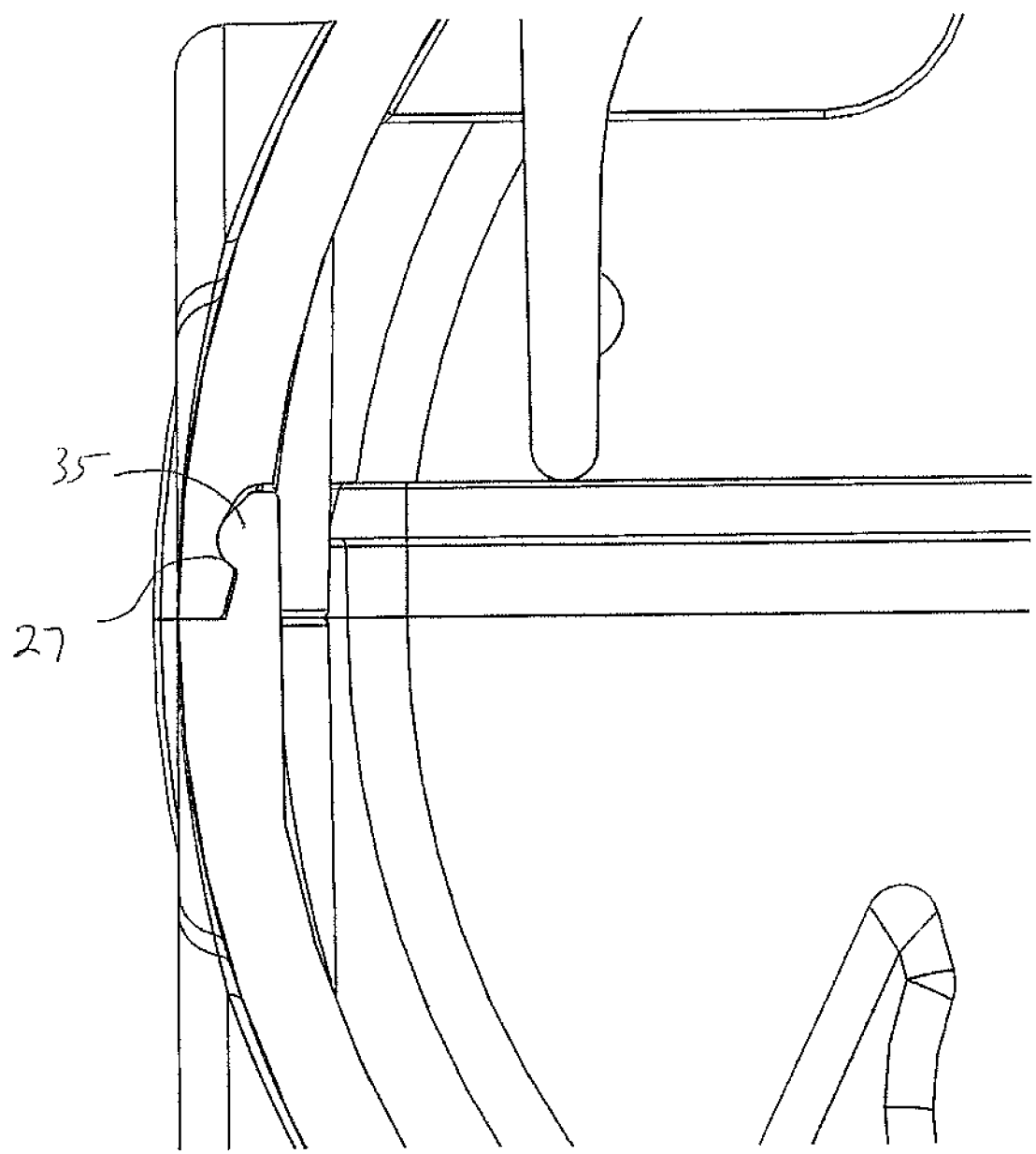
FIG. 15 is a cross-section through a closure latch.

Case 10, FIGS. 1-18, has a clamshell-type construction with first portion or half 20 and second portion of half 30 that are connected by living hinge 40. The halves may each be generally semi-cylindrical so that the closed case is generally cylindrical as shown in the drawings. A positive closure of the two halves is accomplished in this example using closure/latch tabs 33 and 34 in one half 30 that have enlarged ends 35 and 36 (FIG. 8) which fit into tab end receiving depressions 27 and 28 (FIG. 6) in the mating portions of half 20. Opening/closing flange 50 comprising flange halves 51 and 52 allows the user to manipulate the case into the open or closed position. From the closed position shown in FIG. 2 the user can push outward or pull apart on the flange halves 51 and 52 (e.g., with both thumbs, or a finger and thumb of one hand) so as to release the closure tabs from the tab receiving depressions and allow the case to swing open via the living hinge.

Figure 6:
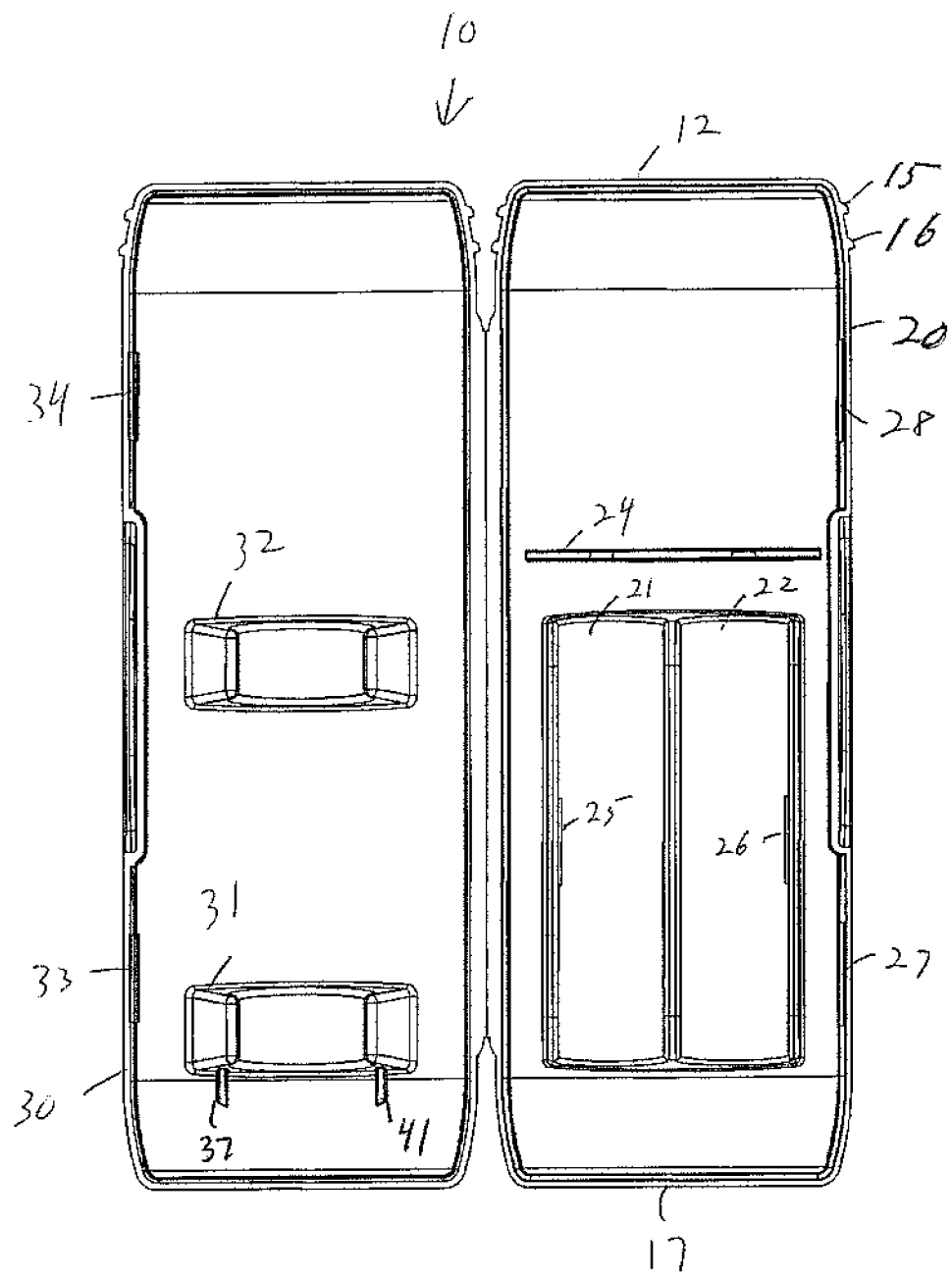
FIG. 6 is a top view of the inside of the case in the open position.
Figure 7:
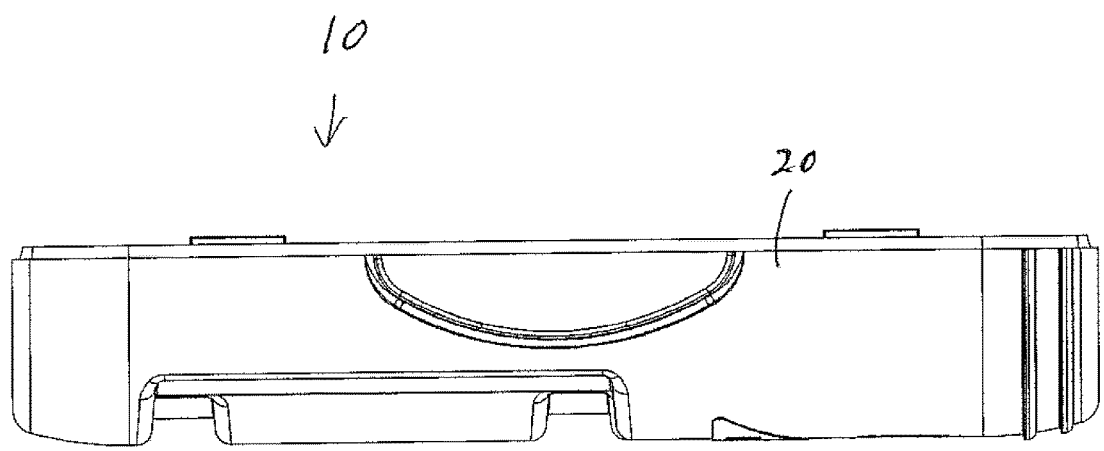
FIG. 7 is a right side view of the outside of the case in the open position.
Figure 16:
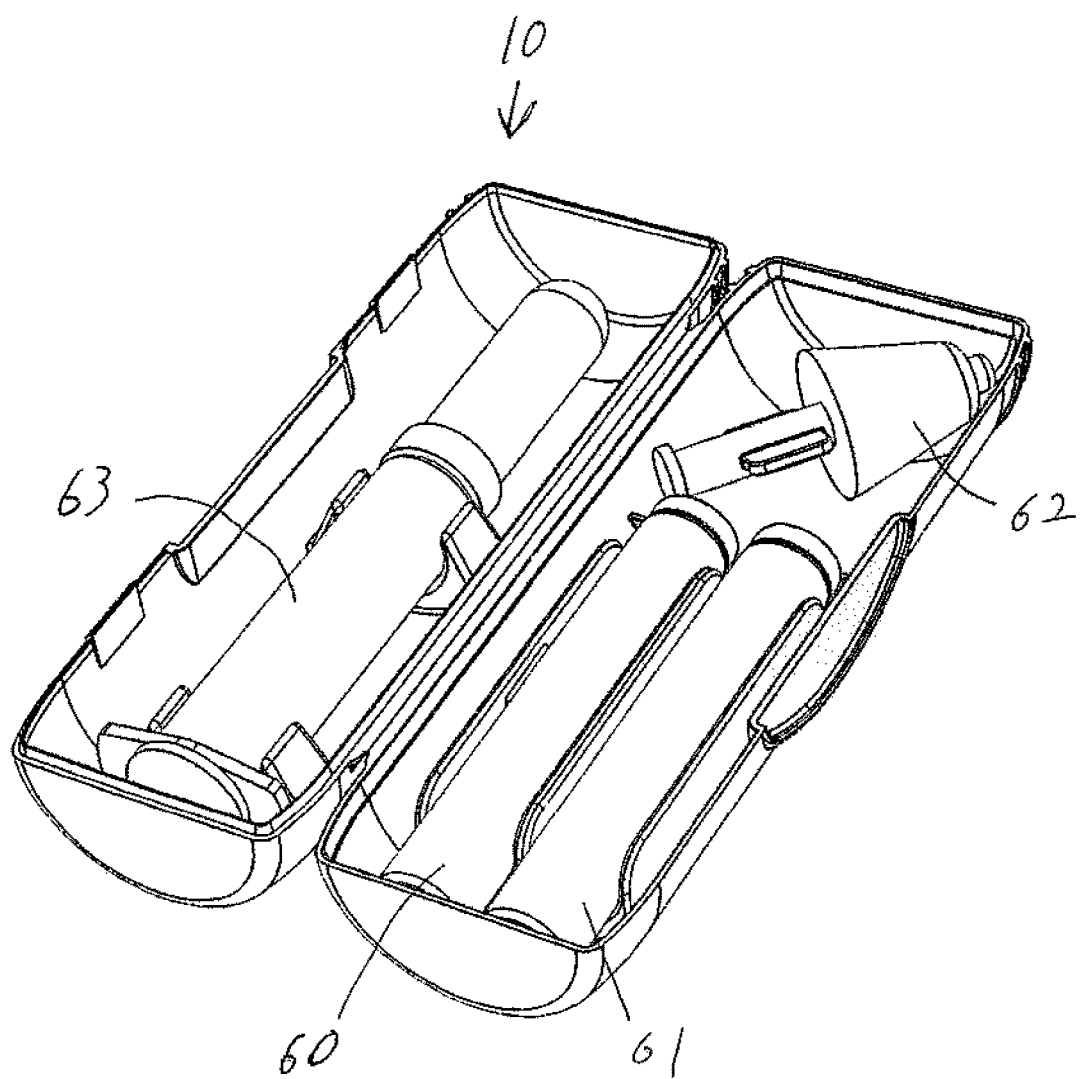
FIG. 16 shows the case open and holding the medicine vials and applicators.

Case half 20 includes vial holders (saddles) 21 and 22 (FIG. 5), each of which is constructed and arranged to hold a 2 milliliter glass vial of naloxone (60 and 61, FIG. 16). The saddles can have another size/shape to hold different size, shape or volume vials. Case 10 includes two essentially identical vial holders 21 and 22 in case two vials are necessary, but only one, or more than two, vial holders could be included, depending on the medicine that is to be carried in the case. Saddles 21 and 22 each include at least one small projection 25 and 26, respectively (FIG. 6). Projections 25 and 26 are located such that they sit above the center of the cylindrical vial when the vial is pushed into the saddle so that the vial is positively retained in the saddle. Since the plastic of the saddle can be flexed, the vial can be removed by grasping it and pulling it out of the saddle. Upstanding wall 24 (FIG. 5) (which sits close to the ends of the vials (not shown in this drawing)) in part defines an empty cavity 29 within the upper part of half 20 that can be used to store a nasal atomizer or other medicine atomizer/applicator (e.g., applicator 62, FIG. 16), which can be stored in its protective plastic wrap in order to maintain sterility. Wall 24 also prevents the vials from sliding into cavity 29.

Figure 18:
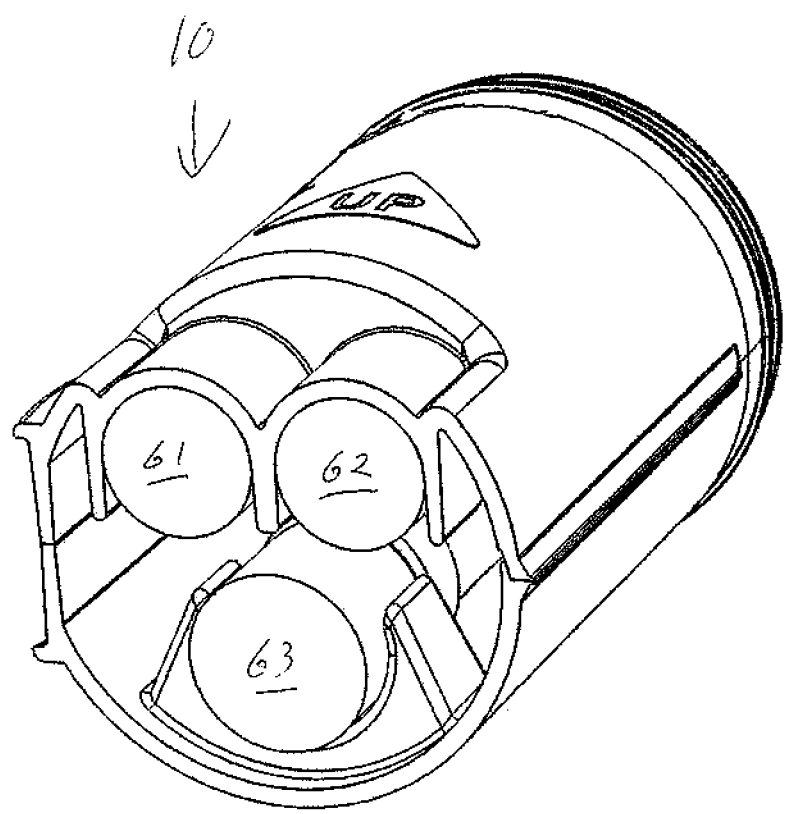
FIG. 18 is a cross-sectional view of the closed case holding the medicine vials and applicators.

Case half 30 includes spaced, longitudinally-aligned saddles 31 and 32 that are constructed and arranged to hold a medicine applicator (e.g., medicine applicator 63, FIG. 16) that can be used to inject the medicine. These saddles are slightly deformed when a medicine applicator barrel is pushed into them so that they tightly grip the medicine applicator barrel. Saddles 31 and 32 also encompass more than 180° of the medicine applicator barrel as shown in FIG. 18 so that the medicine applicator is positively retained in the saddles. Generally triangular tabs 37 and 41 located just behind saddle 31 help to constrain movement of the applicator when it is pulled out of the saddles so that it pushed away from the side of the case half 30 rather than toward the side of the case; the applicator is thus less likely to bind in the saddle. Case half 30 also includes a thin upstanding end peripheral wall 38 (FIG. 10) that facilitates proper alignment of the case halves during closure by sitting just inside of the upper periphery 39 of case half 20 when the case is closed.

Case 10 has top 12 and bottom 14. Bottom 14 has flat end surface 17 (FIG. 1) that allows the case to stand up on a flat surface, while top 12 is more rounded so that the case doesn't easily stand on its top end. This feature helps to keep the case upright when it is set upright on bottom 14, which minimizes the chances of the medicines being spilled. Also, the bottom end of the case has a taper 18 leading to bottom surface 17. This taper helps the case to be more easily inserted into and removed from its holder or pouch (not shown). Top 12 includes circumferential projecting spaced rings 15 and 16 that provide good finger grips to allow the case 10 to be grasped and removed from the pouch. Also, the rings provide a surface on which the case will roll almost in a circle if it is dropped on the ground instead of rolling away from the user.

Figure 17:
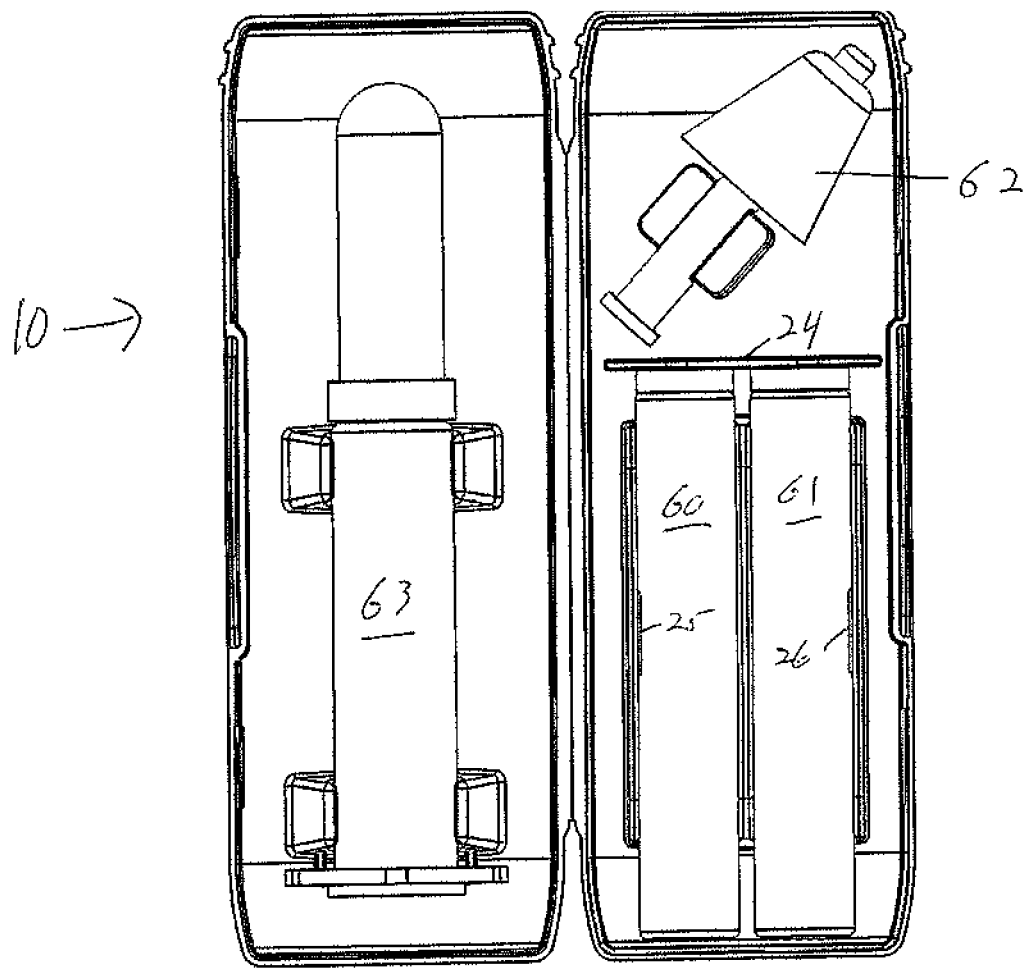
FIG. 17 is a top view of the case open and holding the medicine vials and applicators.

FIGS. 16 through 18 show case 10 with two vials of naloxone 60 and 61, a nasal applicator/atomizer 62, and a medicine applicator (with a needle protective cap) 63.

FIGS. 19 and 20 illustrate a variation of the closure system. Latch tab 33 has the same construction and fit into depression 27 as set forth above. In this example, though, additional external guide tabs 84 and 85 are located just outboard of latch tab 33 and on either side of it. Guide tabs 84 and 85 fit just outside of posts 86 and 87 to help properly align and seat latch tab 33 in depression 27, whereby rim 81 sits on top of ledge 82. The second tab/depression (not shown in FIGS. 19 and 20) can have the same construction.

A number of implementations have been described. Nevertheless, it will be understood that additional modifications may be made without departing from the scope of the inventive concepts described herein, and, accordingly, other embodiments are within the scope of the following claims.

What is claimed is:

1. A clamshell case comprising:
   two portions, a first portion and a second portion that are connected by a hinge, wherein the first portion comprises one or more structures that are each adapted to removably hold a medicine vial, and wherein the second portion comprises one or more structures that are each adapted to removably hold a barrel of a medicine applicator;
   a releasable case closure system that releasably maintains the two portions in an abutting closed position such that an interface between the two portions and the hinge share a closure plane;
   a case opening/closing flange comprising a flange part on each of the two portions;
      wherein the flange parts protrude from the two portions;
      wherein the flange parts circumscribe a flange area when the case is closed; and
   a latch system that holds the two portions in the abutting closed position;
   wherein the case is configured to be opened by applying a prying force upon each flange part from within the flange area, away from the closure plane to release the two portions from the abutting closed position, allowing the case to open via the hinge.

2. The clamshell case of claim 1, wherein the latch system comprises a pair of latch tabs that have enlarged ends and are in one of the two portions, and a pair of tab end receiving structures in mating parts of the other of the two portions.

3. The clamshell case of claim 2, wherein the latch system further comprises a pair of guide tabs located outside of and on either side of each latch tab.

4. The clamshell case of claim 3, wherein the latch system further comprises a pair of posts proximate each tab receiving structure, where when the case is closed the guide tabs fit just outside of the posts to help properly align and seat the latch tab in the tab receiving structure.

5. The clamshell case of claim 1, wherein the structures that are each adapted to removably hold a medicine vial each comprises a saddle.

6. The clamshell case of claim 5, comprising two essentially identical saddle vial holders that each comprises at least one small projection that is located such that it sits above the center of the vial when the vial is pushed into the saddle so that the vial is positively retained in the saddle.

7. The clamshell case of claim 1, wherein the structures that are each adapted to removably hold the barrel of a medicine applicator each comprises a saddle.

8. The clamshell case of claim 7, comprising two spaced aligned saddles that are each adapted to removably hold the barrel of a medicine applicator, wherein the saddles are constructed and arranged to hold a medicine applicator that can be used to inject the medicine, wherein the saddles are slightly deformed when a medicine applicator barrel is pushed into them so that they tightly grip the medicine applicator, and wherein the saddles encompass more than 180° of the medicine applicator barrel so that the medicine applicator is positively retained in the saddles.

9. The clamshell case of claim 1 further comprising an upstanding wall that in part defines an empty cavity that can be used to store a nasal atomizer or other medicine atomizer or applicator.

10. The clamshell case of claim 1, further comprising a case top and a bottom, wherein the bottom has an essentially flat surface that allows the case to stand up on a flat surface, and wherein the top is more rounded than the bottom so that the case doesn't easily stand on its top end.

11. The clamshell case of claim 10, wherein the bottom end of the case has a taper leading to the essentially flat bottom surface, where the taper helps the case to be more easily inserted into and removed from a holder or pouch.

12. The clamshell case of claim 10, wherein the top includes one or more circumferential projecting rings that provide finger grips to allow the case to be grasped and removed from the holder or pouch, and wherein the rings provide a surface on which the case will roll generally in a circle if it is dropped on the ground, instead of rolling away from the user.

13. The clamshell case of claim 1, wherein each portion is generally semi-cylindrical.

14. The clamshell case of claim 1, wherein the opening/closing flange is elliptically shaped when the two portions are in the abutting closed position.

15. A clamshell case comprising:
   two portions, a first portion and a second portion that are connected by a living hinge, wherein the first portion comprises one or more saddles that are each adapted to removably hold a medicine vial, and wherein the second portion comprises one or more saddles that are each adapted to removably hold a barrel of a medicine applicator;
   a releasable case closure system that releasably maintains the two portions in an abutting closed position such that an interface between the two portions defines a closure plane which includes the hinge;
      wherein the closure system comprises a latch system that comprises a pair of latch tabs that have enlarged ends and are in one of the two portions, and a pair of tab end receiving structures in mating parts of the other of the two portions; and
      wherein the latch system holds the two portions in the abutting closed position;
   an upstanding wall that in part defines an empty cavity that can be used to store a nasal atomizer or other medicine atomizer or applicator; and
   a case opening/closing flange comprising a flange part on each of the two portions;
   wherein the flange parts protrude from the two portions;
   wherein the flange parts circumscribe a flange area when the case is closed; and
   wherein the case is configured to be opened by applying a prying force upon each flange part from within the flange area, away from the closure plane to release the two portions from the abutting closed position, allowing the case to open via the hinge.

16. The clamshell case of claim 15, comprising two essentially identical saddle vial holders that each comprise at least one small projection that is located such that it sits above the center of the vial when the vial is pushed into the saddle so that the vial is positively retained in the saddle.

17. A clamshell case comprising:
   two portions, a first generally semi-cylindrical portion and a second generally semi-cylindrical portion that are connected by a living hinge;
   wherein the first portion comprises two saddles that are essentially identical saddle vial holders that are each adapted to removably hold a medicine vial and that each comprise at least one small projection that is located such that it sits above the center of the vial when the vial is pushed into each saddle so that the vial is positively retained in each saddle;
   wherein the second portion comprises two spaced, aligned saddles that are each adapted to removably hold a barrel of a medicine applicator, wherein the saddles are constructed and arranged to hold a medicine applicator that can be used to inject the medicine, wherein the saddles are slightly deformed when a medicine applicator barrel is pushed into them so that they tightly grip the medicine applicator, and wherein the saddles encompass more than 180° of the medicine applicator barrel so that the medicine applicator is positively retained in the saddles;
   a releasable case closure latch system that releasably maintains the two portions in a closed position, wherein the latch system comprises a pair of latch tabs that have enlarged ends and are in one of the two portions, and a pair of tab end receiving structures in mating parts of the other of the two portions, wherein the latch system further comprises a pair of guide tabs located outside of and on either side of each latch tab and a pair of posts proximate each tab receiving structure, where when the case is closed the guide tabs fit just outside of the posts to help properly align and seat the latch tab in the tab receiving structure;
   a case opening/closing flange comprising flange parts on each of the two portions, wherein the opening/closing flange allows the user to manipulate the clamshell case into the open or closed position, wherein from the closed position the user can push the flange parts apart in order to release closure tabs from tab receiving depressions to allow the clamshell case to open via the hinge;
   a top and a bottom, wherein the bottom has an essentially flat surface that allows the case to stand up on a flat surface, wherein the top is more rounded than the bottom so that the case doesn't easily stand on its top end, wherein the bottom end has a taper leading to the essentially flat bottom surface, where the taper helps the case to be more easily inserted into and removed from a holder or pouch, and wherein the top includes one or more circumferential projecting rings that provide finger grips to allow the case to be grasped and removed from the holder or pouch, and wherein the rings provide a surface on which the case will roll generally in a circle if it is dropped on the ground, instead of rolling away from the user; and
   an upstanding wall that in part defines an empty cavity that can be used to store a nasal atomizer or other medicine atomizer or applicator.

* * * * *